(12) United States Patent
Pollock

(10) Patent No.: US 8,062,360 B2
(45) Date of Patent: Nov. 22, 2011

(54) INTRAOCULAR LENS INJECTOR AND METHOD

(75) Inventor: David P. Pollock, Victor, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 349 days.

(21) Appl. No.: 12/137,009

(22) Filed: Jun. 11, 2008

(65) Prior Publication Data
US 2009/0312767 A1 Dec. 17, 2009

(51) Int. Cl.
*A61F 2/16* (2006.01)
(52) U.S. Cl. ...................... 623/6.12; 606/107
(58) Field of Classification Search .......... 606/107, 606/108, 139, 142, 143; 623/5.11, 6.12; 351/160 R, 247
See application file for complete search history.

(56) References Cited

U.S. PATENT DOCUMENTS

| | | | |
|---|---|---|---|
| 5,275,623 A | 1/1994 | Sarfarazi | |
| 6,423,094 B1 | 7/2002 | Sarfarazi | |
| 6,488,708 B2 | 12/2002 | Sarfarazi | |
| 6,761,737 B2 | 7/2004 | Zadno-Azizi et al. | |
| 6,858,040 B2 | 2/2005 | Nguyen et al. | |
| 7,645,300 B2 * | 1/2010 | Tsai | 623/6.12 |
| 2003/0130732 A1 | 7/2003 | Sarfarazi | |
| 2004/0015236 A1 | 1/2004 | Sarfarazi | |
| 2004/0160575 A1 | 8/2004 | Ayton et al. | |
| 2005/0165410 A1 | 7/2005 | Zadno-Azizi et al. | |
| 2005/0182419 A1 | 8/2005 | Tsai | |
| 2005/0228401 A1 | 10/2005 | Zadno-Azizi et al. | |
| 2005/0267575 A1 | 12/2005 | Nguyen et al. | |

* cited by examiner

*Primary Examiner* — S. Thomas Hughes
*Assistant Examiner* — Jonathan W Miles
(74) *Attorney, Agent, or Firm* — Jeffrey Powers

(57) ABSTRACT

An injector and method for injecting a dual optic AIOL into an eye wherein the AIOL is loaded into the injector in an initially loaded condition with the first and second optics in generally coaxial alignment. A lens moving element is provided and operable to move the first optic toward the proximal end of the main body whereupon the first optic becomes located proximally of the second optic. A stop may be provided to prevent the second optic from moving proximally with the first optic. Displacing the optics to a non-coaxial position reduces the cross-sectional area of the AIOL which allows the AIOL to non-destructively compress to the size of the opening of the injector tip which may be as small as about 2.8 mm or less, for example.

6 Claims, 3 Drawing Sheets

INTRAOCULAR LENS INJECTOR AND METHOD

BACKGROUND OF THE INVENTION

The present invention generally relates to intraocular lens ("IOL") injectors, and more particularly relates to an injector and method for facilitating injection of an accommodating intraocular lens (hereinafter "AIOL") having two lenses into an eye.

AIOLs having two optics interconnected by one or more flexible haptics are known, an example of which may be seen in FIG. 1 hereof. While dual optic AIOLs are relatively new, single optic IOLs have been around for decades. Most of the IOL injector art has therefore been developed around the single optic IOL. A common injector design for delivering a single optic IOL into an eye includes a main body having a lumen extending between distal and proximal ends of the main body. A plunger is received at the proximal end of the body and telescopes within the lumen in the manner of a syringe. A tip is provided at the distal end of the injector body and gradually tapers to an opening wherethrough the IOL is expressed from the injector. A single optic IOL is placed inside the lumen and the plunger is advanced to engage and push the IOL through and out the tip. The IOL is made of a material allowing the IOL to compress as it is advanced through the narrowing walls of the tip. As such, the tip opening may be made very small, e.g., about 3 mm or less, which in turn allows for entry of the tip through a smaller incision in the eye. A sub 3 mm incision allows for faster recovery and has become the standard in the cataract surgery field.

AIOLs having two optics generally cannot be used in injectors that have been designed for single optic IOLs described above. IOL injectors are designed to control the interface between the IOL and the plunger. Absent such control, the delicate IOL would likely be damaged during delivery through the injector and rendered useless. Thus, injectors designed for single optic IOLs would probably damage a dual optic AIOL since such an injector would not have precise control over the optic/plunger interface. Injectors specifically designed for dual optic IOLs may be seen in published patent application US 2005/0182419 A1 to George Tsai, published Aug. 18, 2005, and US 2004/0160575 A1 to Ian Ayton et al, published Aug. 19, 2004.

In the Tsai application, an injector is provided having a main body with a plunger and an actuator 104 having a pair of pins 106, 108 which engage the bottom optic. The actuator is manually telescoped along the main body which causes the bottom optic to advance within the lumen of the main body while the upper optic trails along behind the bottom optic. Further advancement of the actuator urge a pair of compacting members 130, 132 forward along with the IOL and actuator. The compacting members also move toward each other to compact, crush and/or fold the IOL. The actuator may then be removed and discarded from the injector main body (see paragraph [0039] thereof) and a plunger is advanced to express the IOL from the injector tip. In another embodiment seen in FIGS. 13-15 thereof, the actuator is in the form of a polymer strip which pulls the bottom optic forward due to the frictional engagement therebetween. In each embodiment, as the first optic is moved forward, the second optic engages an inclined portion of the housing which forces the first optic rearward and downward relative to the advancing second optic. As such, the optics become displaced relative to each other in a flatter, non-coaxial arrangement (see paragraphs [0035] and [0036] thereof).

In the Ayton et al application, the injector includes a pair of opposing engagement faces 212, 242 which are generally flat and constructed from a material to which the outer faces of the viewing elements 122, 124 will self-adhere. The upper engagement surface is advanced forward and downward to pull the optic therealong and displace one optic relative to the other optic. The upper lens compactor having engagement surface 242 is then advanced laterally to "crush" the IOL into a second compacted condition shown in FIG. 18 thereof.

In both the Tsai and Ayton et al publications, one of the optics is engaged and moved in a distal direction toward the tip of the injector to relatively displace the optics. The injectors have many parts to execute the movement necessary to first displace the optics to a non-coaxial position, and then compact the optics for subsequent delivery through the injector tip. The number of parts required for the Tsai and Ayton et al injectors greatly increases the complexity of manufacture and assembly of the injector which adds to the cost thereof. Furthermore, each injector requires at least two separate manipulations to first displace and then compact the optics prior to advancement by the plunger. The more injector manipulations required, the more time needed for the IOL implantation procedure which decreases the efficiency of the procedure.

There thus still exists a need for an dual optic AIOL injector that is relatively easy to manufacture, assemble and use. One or more embodiments of the present invention addresses these and other needs.

SUMMARY OF THE INVENTION

In one embodiment, the present invention provides an injector for delivering a dual optic AIOL into an eye. The injector includes a main body having a lumen extending between proximal and distal ends. A tip is provided at the distal end and includes a lumen terminating at an opening wherethrough the AIOL is expressed from the injector and into an eye. A plunger is inserted into the proximal end of the main body and telescopes within the lumen in the manner of a syringe. The AIOL is loaded into the lumen in an initially loaded condition wherein the first and second optics are generally in coaxial alignment. An optic displacing element is provided and operable to move the first optic toward the proximal end of the main body whereupon the first optic becomes located proximally of the second optic. A stop may be provided to prevent the second optic from moving proximally with the first optic. Displacing the optics to a non-coaxial condition reduces the cross-sectional area of the AIOL which allows the AIOL to non-destructively compress to the size of the opening of the injector tip which may be as small as about 2.8 mm or less, for example.

The tip may be a separate component which is attachable to the distal end of the main body. The distal end of the injector main body lumen may include a lens mounting surface adapted for placement of the AIOL thereon in the initially loaded condition. A cover may be provided movable between open and closed positions relative to the lens mounting surface. In the open position of the cover, the lens mounting surface is accessible for placing the AIOL thereon. The cover may then be closed and the tip may be attached to the distal end of the injector main body. The lens moving element may be formed as a projection within the tip lumen and positioned to move the first optic in a proximal direction as the tip is attached to the distal end of the injector main body portion.

A ramp may be provided proximally of the lens mounting surface. As the first optic is moved proximally by the lens moving element, the first optic moves along the ramp, coming to rest proximally of the second optic which is considered the delivery condition of the AIOL.

Once the AIOL has been moved from the initially loaded condition to the delivery condition, the plunger may be advanced toward the distal end of the main body portion whereupon it moves the first optic which in turn moves the second optic toward the tip. The distal end of the main body lumen and/or the tip lumen taper inwardly causing the first and second optics to compress as the AIOL is advanced and expressed from the tip.

In another embodiment, the invention provides a method of preparing an intraocular lens having first and second optics for injection into an eye, the method comprising the steps of providing an injector main body portion having proximal and distal ends and a lens mounting surface, loading said intraocular lens onto said lens mounting surface; and moving the first optic toward the injector main body potion proximal end whereby said first optic becomes positioned proximally of said second optic.

The method may further include the step of providing an injector tip having a lumen wherethrough said intraocular lens may travel and be expressed from said injector tip; providing a lens moving element on said injector tip, and attaching said injector tip to said lens mounting surface and thereby causing said lens moving element to move said first optic toward said injector body proximal end.

The method may alternately include the step of providing the lens moving element on said lens mounting surface, and attaching said injector tip to said lens mounting surface and thereby causing said lens moving element to move said first optic toward said injector body proximal end.

The method may further comprise the steps of providing a plunger within said injector body, and advancing said plunger toward said injector body distal end, said plunger operable to push and express said intraocular lens out of said injector tip.

The method may further comprise the steps of providing a ramp proximally of said lens mounting surface, said lens moving element operable to move said first optic up said ramp.

The method may further include the step of providing a stop to prevent the second optic from moving proximally with the first optic.

The present invention, including its one or more embodiments, can be better understood with reference to the following drawings, detailed description and examples, which are included to teach the invention without limiting the scope of the invention.

DETAILED DESCRIPTION

Figure 1:
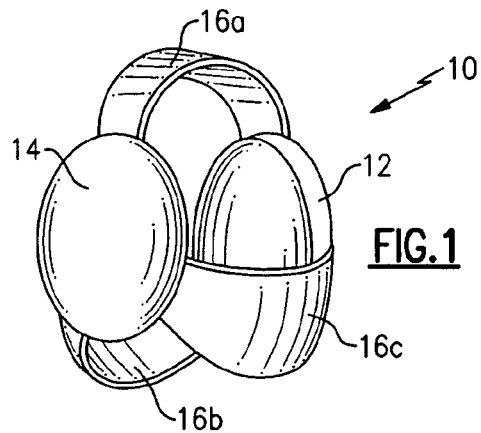
FIG. 1 is a perspective view of a prior art AIOL.

A prior art AIOL 10 is shown in FIG. 1 and includes first and second optics 12, 14, respectively, interconnected by three flexible haptics 16a, b and c. As is well known in the intraocular lens art, AIOL 10 may be made of a hydrophilic or hydrophobic material which may be folded and compressed to deliver the AIOL through the small tip opening of the injector as explained below.

Figure 2:
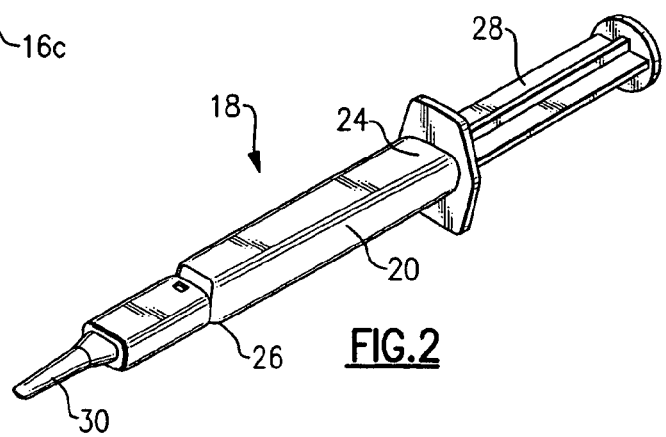
FIG. 2 is a perspective view of an intraocular lens injector according to an embodiment of the invention.

An injector 18 according to an embodiment of the invention is seen in FIG. 2 to include main body portion 20 having a lumen 22 (see FIGS. 4A-C) extending between proximal and distal ends 24, 26 thereof, respectively. A plunger 28 is received in lumen 22 at proximal end 24 of main body portion 20 and operates in the manner of a syringe to express the AIOL 10 from injector tip 30 and into an eye.

Figure 3:
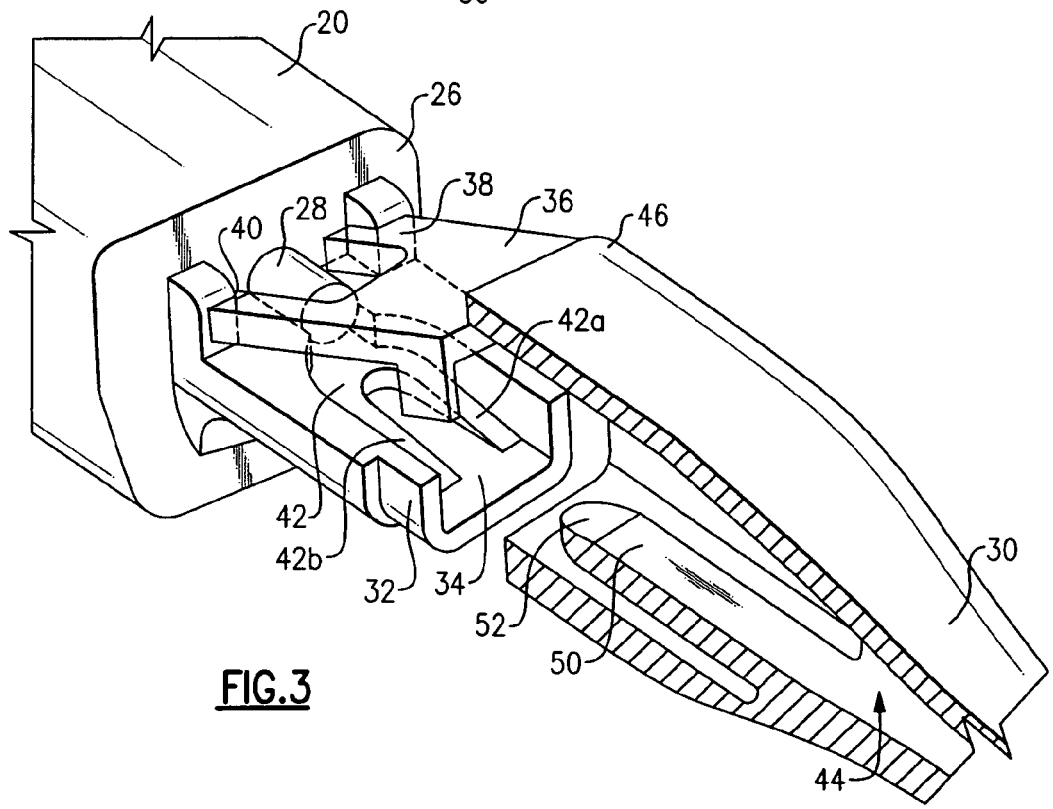
FIG. 3 is an enlarged, fragmented, perspective view of the tip and distal end of the injector main body portion of one embodiment of the invention.
Figure 4A:
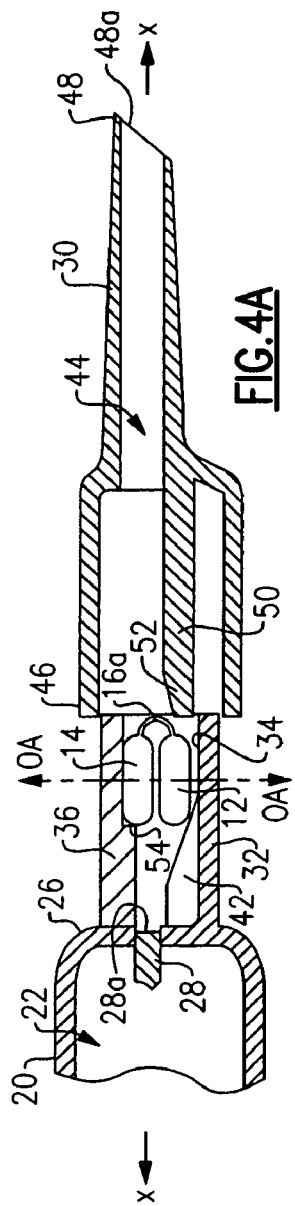
FIG. 4A-C are fragmented, cross-sectional views of the distal end of the injector main body and tip showing the sequential steps of attaching the tip to the distal end of the injector main body portion of the injector of FIG. 2.

Referring to FIG. 3, an embodiment of the invention is seen to include a lens platform 32 extending from main body portion distal end 26. Lens platform 32 includes a lens mounting surface 34 adapted for placing the AIOL 10 thereon in an initially loaded condition seen in FIG. 4A, i.e., lens mounting surface 34 is sized to allow placement of AIOL 10 thereon with first optic 12 and second optic 14 in spaced, generally coaxial alignment along an optical axis OA-OA which extends substantially perpendicular to the longitudinal axis X-X of injector 18 (see FIG. 4A). A cover 36 may be provided which is configured to close over lens platform 32 capturing AIOL 10 therebetween as seen in FIG. 4A. Cover 36 may be pivotally connected to platform 32 via hinge connections 38, 40 (see FIG. 3).

A ramp 42 is provided on lens platform 32 proximally of lens mounting surface 34. Ramp 42 includes an inclined surface which extends proximally and toward longitudinal axis X-X.

In the embodiment of FIGS. 3 and 4A-C, tip 30 is a separate component which is adapted to be connected to injector main body portion 20. Tip 30 includes a lumen 44 extending between proximal and distal ends 46, 48, respectively, with distal end 46 terminating in a small open tip 48a wherethrough the AIOL 10 is expressed from the injector 18 and into an eye. Proximal end 46 is shaped and sized to receive and encase lens platform 32 and cover 36 when in the closed position.

Figure 4B:
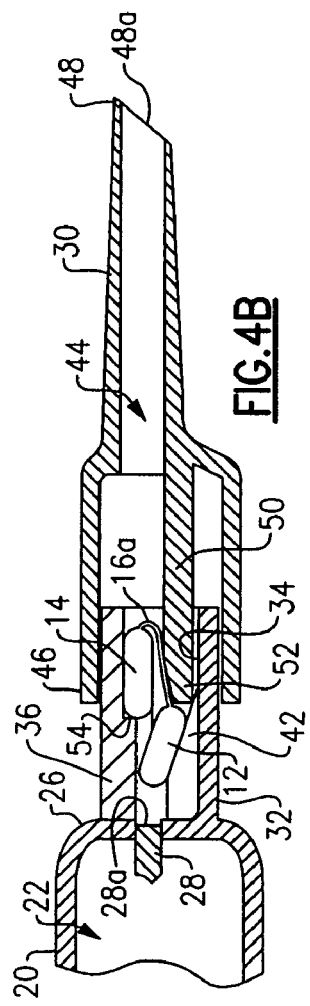

A lens moving element 50 is provided within tip lumen 44 in the form of a finger-like projection extending toward proximal end 46, terminating in a free end 52 which may be tapered. As seen in FIG. 4A, lens moving element 50 is positioned to align with first optic 12 as platform 32 and cover 36 are located to be received in tip proximal end 46. As seen in FIG. 4B, as tip 30 is advanced further toward injector body distal end 26, lens moving element free end 52 abuts first optic 12 and begins moving first optic 12 proximally up ramp 42. Upon full advancement and attachment of tip 30 on lens platform 32 and cover 36, first optic 12 becomes positioned at the top of ramp 42. It will be noticed that as first optic 12 is moved proximally by lens moving element 50, second optic 14 remains substantially stationary such that first optic 12 becomes positioned proximally of second optic 14 and thus no longer in coaxial alignment with first optic 12, i.e., the optical axis OA of first optic 12 becomes off-set from the optical axis OA of second optic 14. This is considered the delivery position in which the overall height and cross-section of AIOL is reduced to allow an optimum compression profile for expression from tip opening 48a. It is noted that although first and second optics 12, 14 are shown in FIG. 4C as slightly overlapping, they may instead become positioned edge to edge or even slightly longitudinally spaced from each other.

To ensure second optic 14 does not move proximally as first optic 12 is moved up ramp 42 by element 50, a stop 54 may be provided in the form of a shoulder provided on the inner surface of cover 36 opposite lens mounting surface 34. In the initially loaded condition of AIOL 10 and closing of cover 36, stop 54 is positioned proximally of second optic 14. As such, stop 54 forms a physical barrier against proximal advancement of second optic 14. Other configurations and locations for stop 54 are of course possible to inhibit proximal advancement of second optic 14.

Figure 4C:
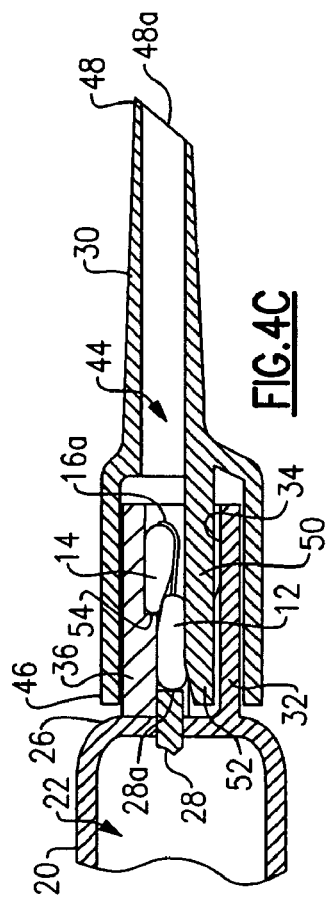

Once tip 30 has been fully attached to main body portion 20 as seen in FIG. 4C, plunger 28 may be advanced within lumen 22 whereupon the plunger tip 28a engages and pushes against first optic 12. Since second optic 14 is positioned distally of first optic 12, both optics are advanced together toward and then expressed from open tip 48a. Tip lumen 44 may taper toward open tip 48a to compress AIOL 10 to the size of open tip 48a.

As seen best in FIG. 3, ramp 42 may be provided in a bifurcated configuration with spaced ramp segments 42a, 42b. The spacing between ramp segments 42a, 42 is such that first optic 12 will span and be supported by both ramp segments 42a, 42b as first optic 12 is moved up ramp 42 by lens moving element 50. Lens moving element free end 52 may be positioned and configured to slide and fit between ramp segments 42a, 42b as tip 30 is attached to lens platform 32 and cover 36. In this way, lens moving element 50 and ramp segments 42a, 42b form a support surface for first optic 12 when AIOL 10 is in the delivery position seen in FIG. 4C. Upon advancing plunger 28, AIOL is moved along the surface of lens moving element 50 which in part defines tip lumen 44.

Figure 5:
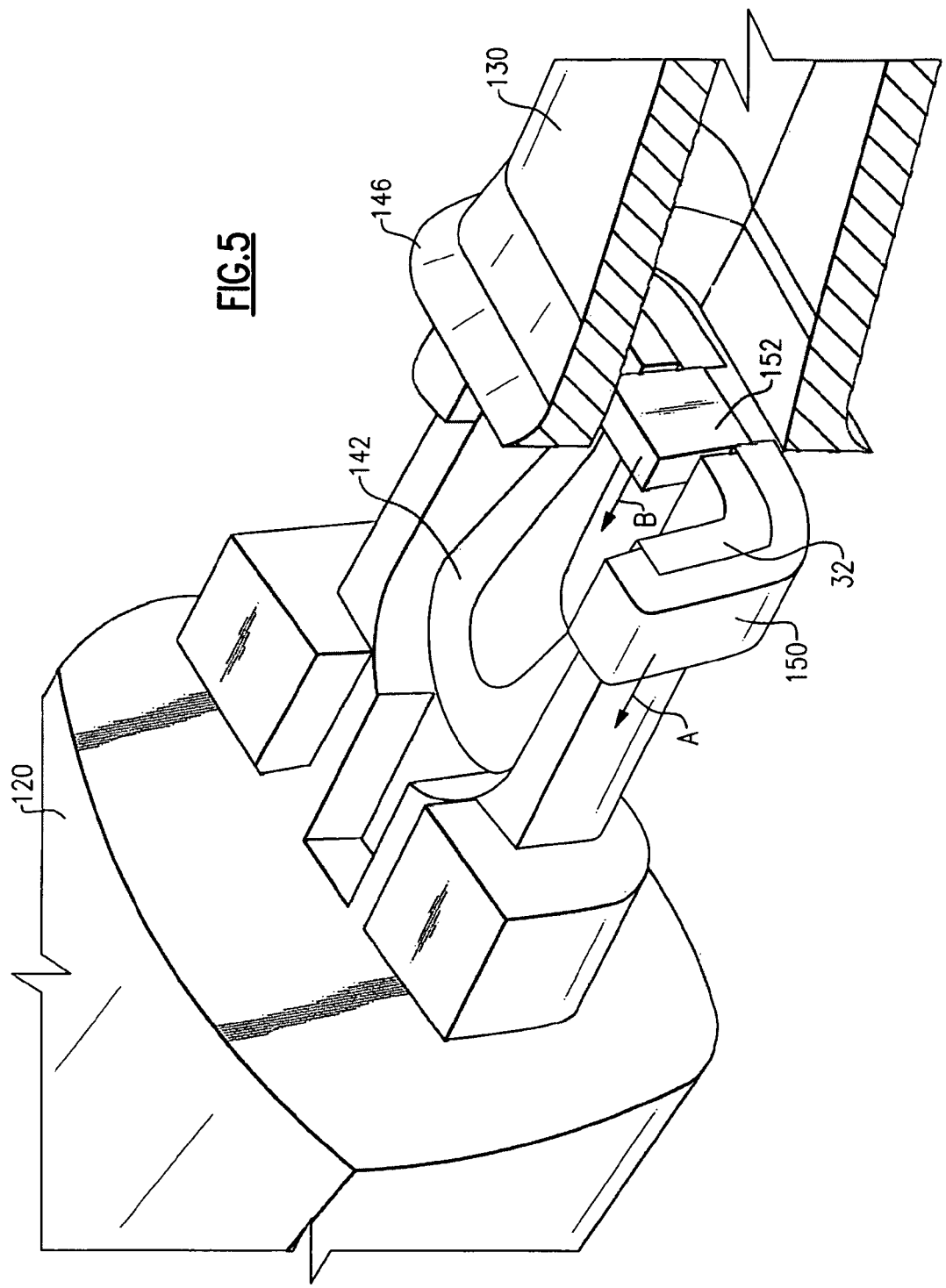
FIG. 5 is an enlarged, fragmented, perspective view of the tip and distal end of the injector main body portion of another embodiment of the invention.

In another embodiment of the invention shown in FIG. 5, the lens moving element is provided on the lens platform 32 in the form of a clip 150 which may slide therealong in the proximal direction as indicated by arrow "A". A projection 152 connects to and moves together with clip 150 as indicated by arrow "B". The proximal end 146 of tip 130 is shaped and sized to align with clip 150 such that as tip 130 is attached to lens platform 32, proximal end 146 moves clip 150 (and hence also projection 152) toward main body portion 120. Projection 152 is operable to move first optic 12 up ramp 142 in the same manner as lens moving element 50 in the embodiment of FIGS. 3 and 4A-C. It is noted no cover similar to cover 36 is shown in FIG. 5 for the sake of clarity.

It will be appreciated that while the invention has been shown and described in relation to two possible embodiments thereof, many changes may be made without departing from the fill spirit and scope of the invention as defined by the claims which follow. For example, the injector tip 30 may be integrally formed with the main body portion of the injector rather than a separately attached component. In this instance, the lens moving element could comprise an element which extends radially through the injector body wall into the lumen. The element may be slidable within a groove provided in the injector body wall toward the proximal end of the injector body whereupon the element engages and moves the first optic proximally of the second optic. The ramp may be provided within the main body lumen proximally of the lens loading area.

As a further example, the lens may be preloaded into the lumen at manufacture so that the doctor does not need to perform this step.

As yet a further example, the lens may be preloaded into a cartridge which is adapted to be received in the injector body. The cartridge may include the lens moving feature such that the lens is moved to its delivery position prior to the cartridge being attached to the injector body.

These and other modifications will be apparent to those skilled in the art.

What is claimed is:

1. An injector for injecting an intraocular lens having first and second optics into an eye, said injector comprising:
   a) an injector main body portion having a lumen extending between a proximal end and a distal end, and including a lens mounting surface adapted for placement of the intraocular lens thereon in an initially loaded condition, an opening at the distal end of the lumen, and a ramp; wherein said ramp is located further from the opening than said lens mounting surface; and
   an injector tip having an opening for delivering the intraocular lens into the eye;
   the injector tip being moveable relative to the injector main body, and the injector tip having a lumen extending between an injector tip proximal end and an injector tip distal end, said injector tip proximal end adapted to be connected to the distal end of said injector main body portion;
   said injector tip comprising a lens moving element operable to move said first optic along said ramp toward said injector body proximal end when the injector tip proximal end is connected to the distal end of said injector main body portion.

2. The injector of claim 1 wherein said lens moving element is positioned within said injector tip lumen.

3. The injector of claim 2 wherein said lens moving element comprises a projection positioned to move said first optic along said ramp toward said injector body proximal end as said injector tip is connected to said injector main body portion.

4. The injector of claim 3 wherein said ramp includes first and second spaced ramp segments, said lens moving element adapted to extend between said first and second ramp segments.

5. The injector of claim 1 and further comprising a stop positioned opposite said ramp, said stop operable to block said second optic from advancing toward said main body portion proximal end as said first optic is moved by said lens moving element.

6. The injector of claim 5 and further comprising a cover configured to be placed over said lens mounting surface, said stop located on said cover.

* * * * *